(12) United States Patent
Moloney-Egnatios

(10) Patent No.: US 10,453,562 B2
(45) Date of Patent: Oct. 22, 2019

(54) CONSUMER-ORIENTED BIOMETRICS DATA MANAGEMENT AND ANALYSIS SYSTEM

(71) Applicant: ProductVisionaries, LLC, Los Altos, CA (US)

(72) Inventor: Kate Moloney-Egnatios, Los Altos, CA (US)

(*) Notice: Subject to any disclaimer, the term of this patent is extended or adjusted under 35 U.S.C. 154(b) by 409 days.

(21) Appl. No.: 14/273,266

(22) Filed: May 8, 2014

(65) Prior Publication Data
US 2015/0324540 A1   Nov. 12, 2015

(51) Int. Cl.
G16H 10/60 (2018.01)
G16H 50/30 (2018.01)
G16H 50/20 (2018.01)
G16H 10/40 (2018.01)

(52) U.S. Cl.
CPC ............ *G16H 10/60* (2018.01); *G16H 10/40* (2018.01); *G16H 50/20* (2018.01); *G16H 50/30* (2018.01)

(58) Field of Classification Search
CPC ...... G06Q 50/22; G06Q 50/24; G06F 19/322; G06F 19/323–327; G06F 19/30; G06F 19/32; G06F 19/34; G06F 19/3475; G06F 19/36; G16H 10/00; G16H 10/60; G16H 15/00; G16H 20/00; G16H 20/60; G16H 20/70; G16H 50/00; G16H 50/30; G16H 50/50; G16H 50/70; G16H 50/80; G16H 80/00
USPC .......................................................... 705/2, 3
See application file for complete search history.

(56) References Cited

U.S. PATENT DOCUMENTS

| | | | |
|---|---|---|---|
| 7,039,628 B2 | 5/2006 | Logan, Jr. | |
| 7,855,177 B1* | 12/2010 | Wahren | A61K 38/28 514/1.1 |
| 8,121,855 B2 | 2/2012 | Lorsch | |
| 8,626,534 B2 | 1/2014 | Hasan et al. | |
| 9,361,429 B2* | 6/2016 | Otvos | G06F 19/34 |
| 2003/0058245 A1* | 3/2003 | Brazhnik | G16B 5/00 345/440 |
| 2004/0016035 A1* | 1/2004 | Floyd | G01N 33/54393 435/7.5 |
| 2004/0122708 A1 | 6/2004 | Avinash et al. | |
| 2004/0172290 A1* | 9/2004 | Leven | A61B 5/0006 705/2 |

(Continued)

OTHER PUBLICATIONS

Frøslie et alo., Shape information from glucose curves: Functional data analysis compared with traditional summary measures, BMC Medical Research Methodology 2013, 13:6, 15 pages.*

(Continued)

*Primary Examiner* — Jason S Tiedeman
(74) *Attorney, Agent, or Firm* — McDonnell Boehnen Hulbert & Berghoff LLP

(57) ABSTRACT

A set of information including manually entered health-related data for a user, automatically collected health-related data for the user, and test results for the user may be received. In response to receiving the set of information, the manually entered health-related data for the user, the automatically collected health-related data for the user, and the test results for the user may be integrated into a comprehensive health profile for the user. Upon a request made on behalf of the user, at least part of the comprehensive health profile may be provided to the user.

15 Claims, 9 Drawing Sheets

(56) References Cited

U.S. PATENT DOCUMENTS

| | | | |
|---|---|---|---|
| 2004/0267098 A1* | 12/2004 | Moore | A47G 19/2227 600/300 |
| 2005/0113650 A1* | 5/2005 | Pacione | A61B 5/411 600/300 |
| 2005/0159656 A1* | 7/2005 | Hockersmith | A61B 5/14532 600/315 |
| 2005/0203900 A1* | 9/2005 | Nakamura | G06F 16/334 |
| 2006/0136263 A1* | 6/2006 | Fry | G06Q 10/10 705/2 |
| 2006/0167872 A1* | 7/2006 | Parikh | G06F 3/0237 |
| 2006/0205564 A1* | 9/2006 | Peterson | A61B 5/0022 482/8 |
| 2007/0016450 A1 | 1/2007 | Bhora et al. | |
| 2007/0055552 A1* | 3/2007 | St. Clair | G06F 19/3481 705/3 |
| 2007/0078610 A1* | 4/2007 | Adams | G01N 1/10 702/28 |
| 2007/0112598 A1* | 5/2007 | Heckerman | G06Q 50/22 705/2 |
| 2007/0179352 A1* | 8/2007 | Randlov | G16H 15/00 600/300 |
| 2007/0294103 A1* | 12/2007 | Ahmad | G06F 19/327 705/2 |
| 2009/0012716 A1* | 1/2009 | Urdea | G01N 33/48714 702/19 |
| 2009/0069642 A1* | 3/2009 | Gao | A61B 5/02055 600/300 |
| 2009/0150440 A1* | 6/2009 | Buck | G06F 19/3456 |
| 2009/0156924 A1* | 6/2009 | Shariati | A61B 5/14532 600/365 |
| 2010/0063837 A1* | 3/2010 | Bellante | G06Q 10/105 705/2 |
| 2010/0076786 A1* | 3/2010 | Dalton | G06Q 10/00 705/3 |
| 2010/0249531 A1 | 9/2010 | Hanlon et al. | |
| 2010/0317950 A1* | 12/2010 | Galley | G06F 19/322 600/365 |
| 2011/0047108 A1* | 2/2011 | Chakrabarty | G06F 19/3456 706/14 |
| 2011/0245634 A1* | 10/2011 | Ray | A61B 5/0002 600/309 |
| 2011/0257998 A1* | 10/2011 | Cinqualbre | G06Q 50/22 705/3 |
| 2011/0288877 A1 | 11/2011 | Ofek et al. | |
| 2012/0290327 A1* | 11/2012 | Hanlon | G06F 19/3475 705/3 |
| 2012/0328594 A1* | 12/2012 | McKenna | G01N 33/66 424/94.4 |
| 2013/0018671 A1* | 1/2013 | Hussam | G06Q 50/22 705/3 |
| 2013/0289889 A1* | 10/2013 | Yuen | G06F 19/3418 702/19 |
| 2013/0332082 A1* | 12/2013 | Otvos | G06F 19/34 702/19 |
| 2014/0128705 A1* | 5/2014 | Mazlish | A61B 5/4866 600/365 |
| 2014/0200178 A1* | 7/2014 | Varvel | G01N 33/6893 514/5.9 |
| 2014/0303988 A1* | 10/2014 | Maneri | G16H 50/20 705/2 |
| 2014/0324460 A1* | 10/2014 | Caffrey | G01N 33/6893 705/3 |
| 2015/0006456 A1* | 1/2015 | Sudharsan | G06N 5/048 706/46 |

OTHER PUBLICATIONS

European Search Report, European Patent Application No. 15166471. 1, dated Nov. 8, 2017, 8 pages.

* cited by examiner

CONSUMER-ORIENTED BIOMETRICS DATA MANAGEMENT AND ANALYSIS SYSTEM

BACKGROUND

Personal health is a growing market with revenues that can be measured in the hundreds of billions of dollars. Now more than ever, individuals want access to information about, as well as privacy and control over, their personal health. In the traditional health provider model, an individual would visit a health care professional, such as a doctor, and this professional might order tests. The individual would then go to a laboratory to have the tests conducted, and the test results would be provided to the professional. Thus, raw test results and interpretation of these results would be mediated by the professional, rather than being under control of the individual. Further, these results may never make it to the individual at all due to laboratory error, administration error, or human error. Yet further, these results might not be viewed in the context of the individual's overall health.

SUMMARY

Individuals may obtain more control over management of their personal health through the use of an online aggregated health information system. This system, which may include one or more computing devices arranged to communicate over the Internet and/or other networks, may store health information regarding one or more individual users. This information may include biographical information, biometric information, health history, medicines and/or drugs used by the users, tests ordered and test results for the users, nutrition and diet information regarding the users, exercise information regarding the users, the users' answers to various health questionnaires, as well as other types of health-related data.

With these types of information in one centralized location, a user may be able to better manage his or her own health care, rather than rely on various doctors, hospitals, laboratories, web sites, and so on that may not effectively communicate with one another. Further, with the advent of wearable health-tracking devices, such as digital pedometers, heart-rate monitors, blood sugar monitors, and so on, the user may be able to automatically measure a wealth of information regarding his or her body. These measurements may also be integrated into the health information system.

With access to a broad range of personalized data, the health information system may be able to perform analyses on the data to detect correlations and trends that might not be otherwise apparent. Further, the health information system may also be able to serve as an ecommerce portal through which users can browse and order test kits. Results from these tests may be integrated into the user's data in the health information system. Moreover, the health information system may also aggregate health-related information that may be of interest to the user, such as articles, papers, links to web sites, and so on. As a result, the health information system may be tailored to the needs of consumers, and not dependent on particular access devices, information upload devices, health tracking and monitoring devices, medical/health/lifestyle professionals, health or medical tests, laboratories or pharmacies.

Accordingly, in a first example embodiment, a set of information including manually-entered health-related data for a user, automatically collected health-related data for the user, and test results for the user may be received. In response to receiving the set of information, the manually entered health-related data for the user, the automatically collected health-related data for the user, and the test results for the user may be integrated into a comprehensive health profile for the user. Upon a request made on behalf of the user, at least part of the comprehensive health profile may be provided to the user.

A second example embodiment may include a non-transitory, computer-readable storage medium, having stored thereon program instructions that, upon execution by a computing device, cause the computing device to perform operations in accordance with the first example embodiment.

A third example embodiment may include a computing device containing at least a processor and data storage. The data storage may include program instructions that, when executed by the processor, cause the computing device to perform operations in accordance with the first example embodiment.

These as well as other embodiments, aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

DETAILED DESCRIPTION

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Other embodiments can be utilized, and other changes can be made, without departing from the scope of the subject matter presented herein.

Thus, the example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

1. OVERVIEW

Figure 1:
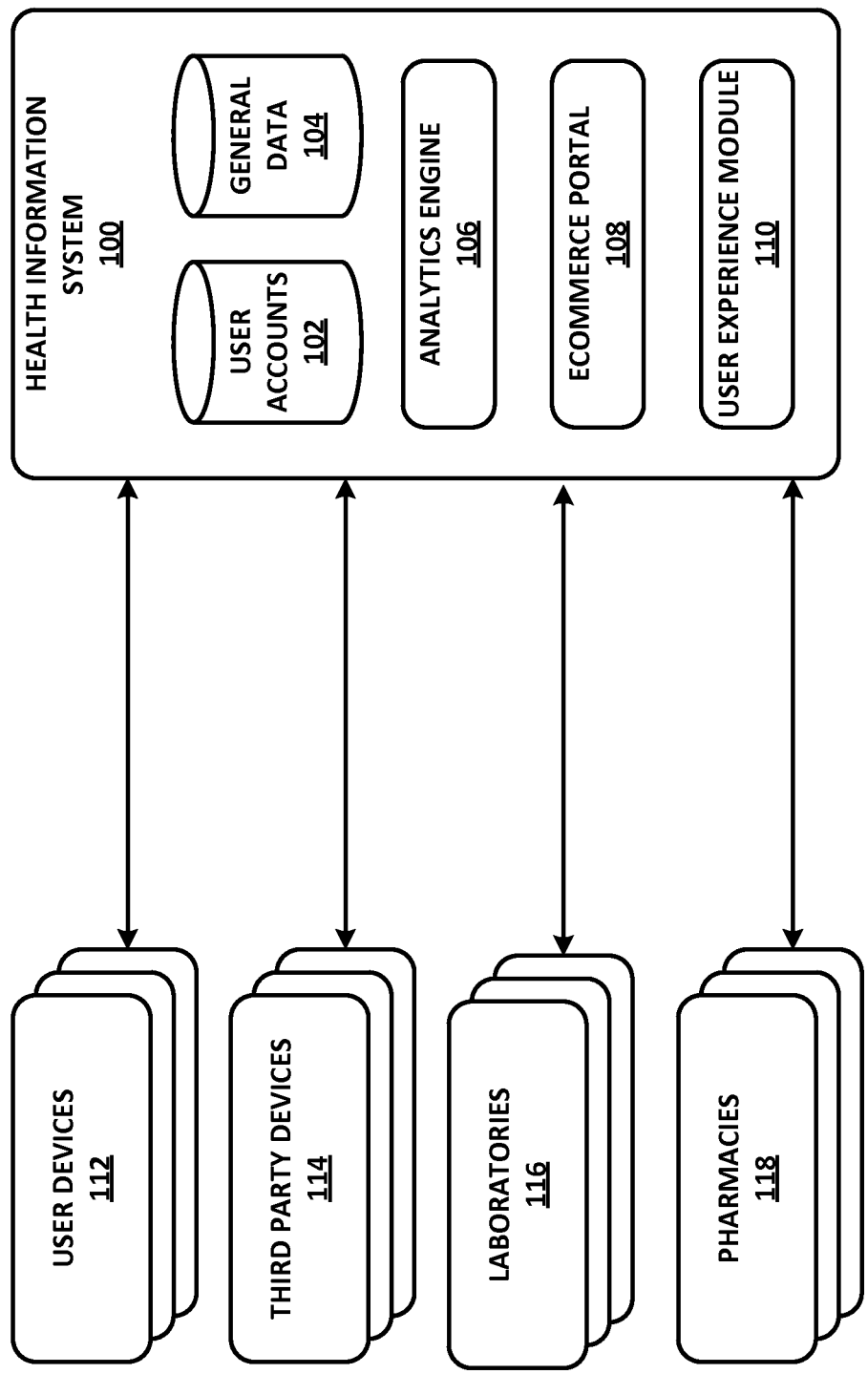
FIG. 1 is a high-level depiction of a health information system, according to an example embodiment.

FIG. 1 is a high-level depiction of a health information system 100 and its connectivity to other entities. Health information system 100 may be software that operates on one or more computing devices, such as client and/or server devices. In some embodiments, health information system 100 may be implemented as a "cloud-based" service on Internet servers, accessible via web pages, for example. In other embodiments, health information system 100 may consist of client and/or server software.

Regardless, health information system 100 may contain or have access to user accounts 102, general data 104, analytics engine 106, ecommerce portal 108, and user experience module 110.

User accounts 102 may be a database and/or some other organization of information that represents attributes of one or more users of health information system 100. Thus, for each user, user accounts 102 may include a username, email address, physical address, phone number, and/or billing information. User accounts 102 may also include representations of health information (such as test results, questionnaire results, and quantitative, biometric data related to user health) and ecommerce transactions (such as test kits ordered) for each user. Users may be able to tag or mark some aspects of their profile as "public" or "semi-private" data that can be shared with a medical professional, family, and/or friends. By default, some or all of a user's data may be marked as "private" until the user marks the data otherwise.

General data 104 may include health-related information that is not specific to a particular user. Thus, general data may include height and weight charts, nutrition and diet information, exercise information, health-related articles, and so on. Users of health information system 100 may access general data 104 at their leisure or when they have a specific health-related question. General data may be browseable and/or searchable.

Analytics engine 106 may be software arranged to calculate correlations between the data associated with a user in user accounts 102. For instance, analytics engine 106 may be able to determine relationships between a user's diet, medications and his or her reported mood. Further, analytics engine 106 may be able to track longitudinal trends related to a user's health. As an example, analytics engine 106 might find a long term trend between a user's weight and one or more of his or her diet, sleep, blood sugar, heart rate, hydration levels, and so on. Analytics engine may also be able to calculate these correlations and longitudinal trends across multiple users.

Ecommerce portal 108 may be an online store that allows users to shop for health-related products and services. For instance, ecommerce portal may provide over-the-counter medicines, health-related books, exercise equipment, vitamins and supplements, specialty food products, specialty health and medical products, mobile application downloads, pet health and pet health products, health tracking and monitoring devices, electronic gadgets, over-the-counter health products, and self-testing products and home test kits.

As an example, for the test kits, the user may order a kit, and have it shipped to the user. The user may perform the test and ship the results to an associate laboratory. After completing the testing procedure, the user may use ecommerce portal 108 to find an appropriate laboratory that can provide test results, or the user may determine a laboratory in some other fashion. The user would ship a sample associated with the test (e.g., a blood sample, saliva sample, skin sample, etc.) to one of the laboratories. The selected laboratory would then receive the sample, perform testing on the sample, and upload and/or post the results to health information system 100, and these results may become part of the user's account in user accounts 102.

User experience module 110 may provide the "front end" or user interface to health information system 100. Thus, user experience module 100 may be arranged to provide users intuitive access to information in their accounts, as well as to general data 104. For instance, a particular user might be able to customize their user experience so that they are provided with more information that they are interested in, and less information of general interest.

Health information system 100 may facilitate online access from one or more user devices 112, third party devices 114, and/or laboratories 116. Each of user devices 112, third party devices 114, and laboratories 116 may be a computing device, and these computing devices may be interconnected by a computer network, such as the Internet or one or more private networks.

Each of user devices 112 may correspond to a human user of health information system 100. Such a user device may be a mobile device, laptop, tablet, PC, etc., that the user utilizes to access health information system 100. Alternatively, some of these user devices may be wearable computing devices, health tracking devices, and/or self-monitoring devices (e.g., digital pedometers, heart rate monitors, blood sugar monitors, etc.) that are configured to upload or post gathered health data to the user's account.

Each of third party devices 114 may correspond to a human or automated entity that is permitted to have at least limited access to some aspects of user accounts 102. For instance, third party devices 114 may be associated with medical professionals who are granted access to test results or other information in one or more of user accounts 102. In some situations, third party devices 114 may include doctors, doctor's assistants, hospitals, clinics, and so on, and/or devices or software (e.g., mobile devices, laptops, tablets, PCs, applications, etc.) used by these individuals or organizations.

Laboratories 116 may correspond to one or more medical testing laboratories that may be able to, with a user's permission, upload test results to the user's account (e.g., update or post the results to health information system 100 via an appropriate application programming interface (API)). However, other arrangements are possible, such as two or more human users sharing the same user device, two or more medical professionals sharing the same third party device, and so on.

Pharmacies 118 may correspond to one or more online or physical entities that can fulfill prescriptions for medicines and/or drugs. Users may communicate with pharmacies 118 either directly or through health information system 100.

Health information system 100, as well as any other device or function associated with the architecture of FIG. 1, can represent, be operated on, or be operated by one or more computing devices. These computing devices may be organized in a standalone fashion, in networked computing environments, or in other arrangements. Examples are provided in the next section.

2. EXAMPLE COMPUTING DEVICES AND CLOUD-BASED COMPUTING ENVIRONMENTS

Figure 2:
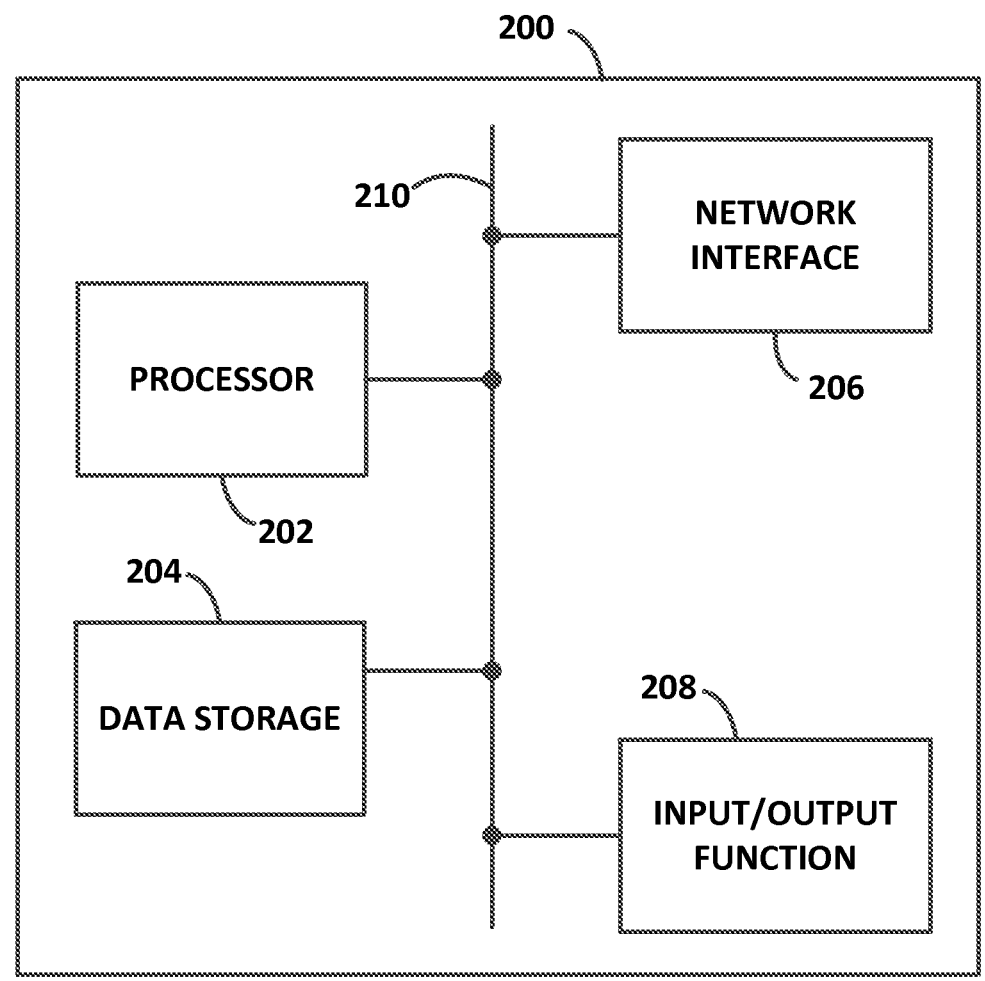
FIG. 2 illustrates a schematic drawing of a computing device, according to an example embodiment.

FIG. 2 is a simplified block diagram exemplifying a computing device 200, illustrating some of the functional components that could be included in a computing device arranged to operate in accordance with the embodiments herein. Example computing device 200 could be a personal computer (PC), laptop, server, or some other type of computational platform. For purposes of simplicity, this specification may equate computing device 200 to a server from time to time. Nonetheless, it should be understood that the description of computing device 200 could apply to any component used for the purposes described herein.

In this example, computing device 200 includes a processor 202, a data storage 204, a network interface 206, and an input/output function 208, all of which may be coupled by a system bus 210 or a similar mechanism. Processor 202 can include one or more central processing units (CPUs), such as one or more general purpose processors and/or one or more dedicated processors (e.g., application specific integrated circuits (ASICs), digital signal processors (DSPs), network processors, etc.).

Data storage 204, in turn, may comprise volatile and/or non-volatile data storage and can be integrated in whole or in part with processor 202. Data storage 204 can hold program instructions, executable by processor 202, and data that may be manipulated by these instructions to carry out the various methods, processes, or functions described herein. Alternatively, these methods, processes, or functions can be defined by hardware, firmware, and/or any combination of hardware, firmware and software. By way of example, the data in data storage 204 may contain program instructions, perhaps stored on a non-transitory, computer-readable medium, executable by processor 202 to carry out any of the methods, processes, or functions disclosed in this specification or the accompanying drawings.

Network interface 206 may take the form of a wireline connection, such as an Ethernet, Token Ring, or T-carrier connection. Network interface 206 may also take the form of a wireless connection, such as IEEE 802.11 (Wifi), BLUETOOTH®, or a wide-area wireless connection. However, other forms of physical layer connections and other types of standard or proprietary communication protocols may be used over network interface 206. Furthermore, network interface 206 may comprise multiple physical interfaces.

Input/output function 208 may facilitate user interaction with example computing device 200. Input/output function 208 may comprise multiple types of input devices, such as a keyboard, a mouse, a touch screen, and so on. Similarly, input/output function 208 may comprise multiple types of output devices, such as a screen, monitor, printer, or one or more light emitting diodes (LEDs). Additionally or alternatively, example computing device 200 may support remote access from another device, via network interface 206 or via another interface (not shown), such as a universal serial bus (USB) or high-definition multimedia interface (HDMI) port.

In some embodiments, one or more computing devices may be deployed in a networked architecture. The exact physical location, connectivity, and configuration of the computing devices may be unknown and/or unimportant to client devices. Accordingly, the computing devices may be referred to as "cloud-based" devices that may be housed at various remote locations.

Figure 3:
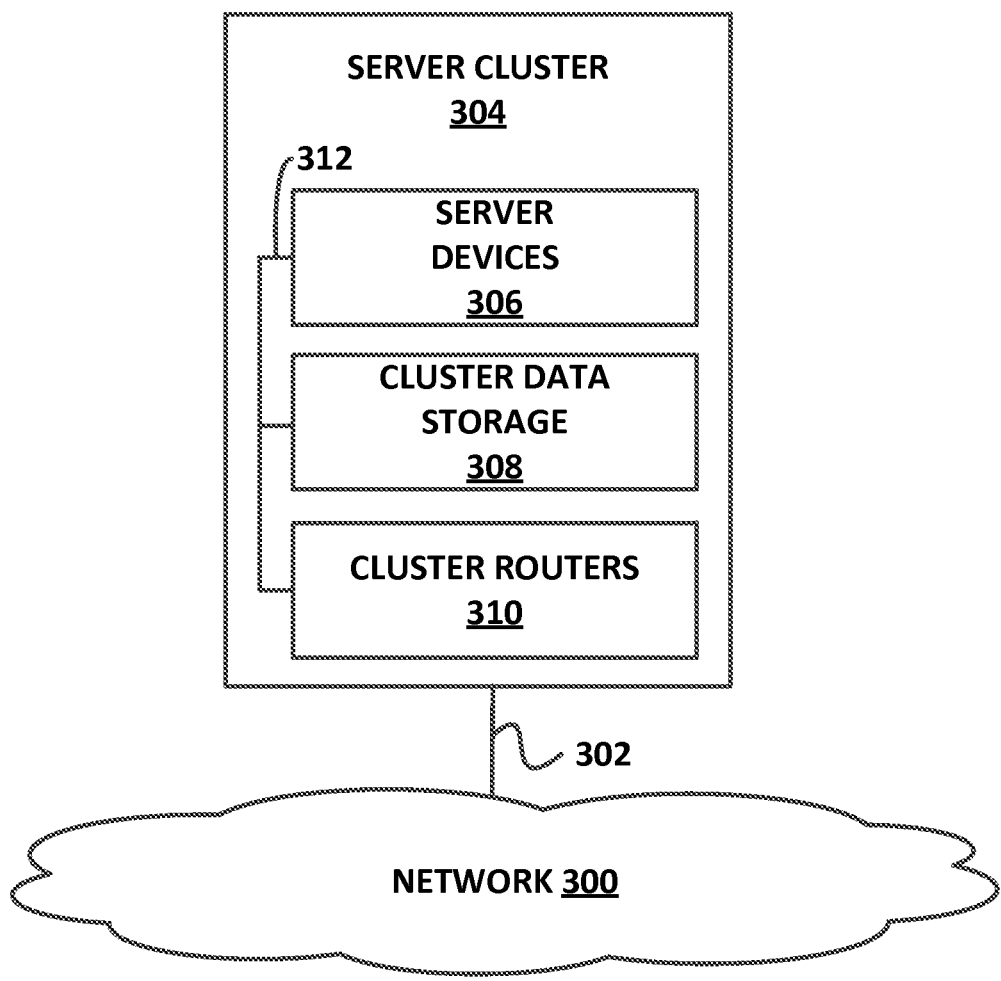
FIG. 3 illustrates a schematic drawing of a networked server cluster, according to an example embodiment.

FIG. 3 depicts a cloud-based server cluster 304 in accordance with an example embodiment. In FIG. 3, functions of computing device 200 may be distributed between server devices 306, cluster data storage 308, and cluster routers 310, all of which may be connected by local cluster network 312. The number of server devices, cluster data storages, and cluster routers in server cluster 304 may depend on the computing task(s) and/or applications assigned to server cluster 304.

For example, server devices 306 can be configured to perform various computing tasks of computing device 200. Thus, computing tasks can be distributed among one or more of server devices 306. To the extent that these computing tasks can be performed in parallel, such a distribution of tasks may reduce the total time to complete these tasks and return a result.

Cluster data storage 308 may be data storage arrays that include disk array controllers configured to manage read and write access to groups of hard disk drives. The disk array controllers, alone or in conjunction with server devices 306, may also be configured to manage backup or redundant copies of the data stored in cluster data storage 308 to protect against disk drive failures or other types of failures that prevent one or more of server devices 306 from accessing units of cluster data storage 308.

Cluster routers 310 may include networking equipment configured to provide internal and external communications for the server clusters. For example, cluster routers 310 may include one or more packet-switching and/or routing devices configured to provide (i) network communications between server devices 306 and cluster data storage 308 via cluster network 312, and/or (ii) network communications between the server cluster 304 and other devices via communication link 302 to network 300.

Additionally, the configuration of cluster routers 310 can be based at least in part on the data communication requirements of server devices 306 and cluster data storage 308, the latency and throughput of the local cluster networks 312, the latency, throughput, and cost of communication link 302, and/or other factors that may contribute to the cost, speed, fault-tolerance, resiliency, efficiency and/or other design goals of the system architecture.

3. EXAMPLE INFORMATION FLOWS

Figure 4A:
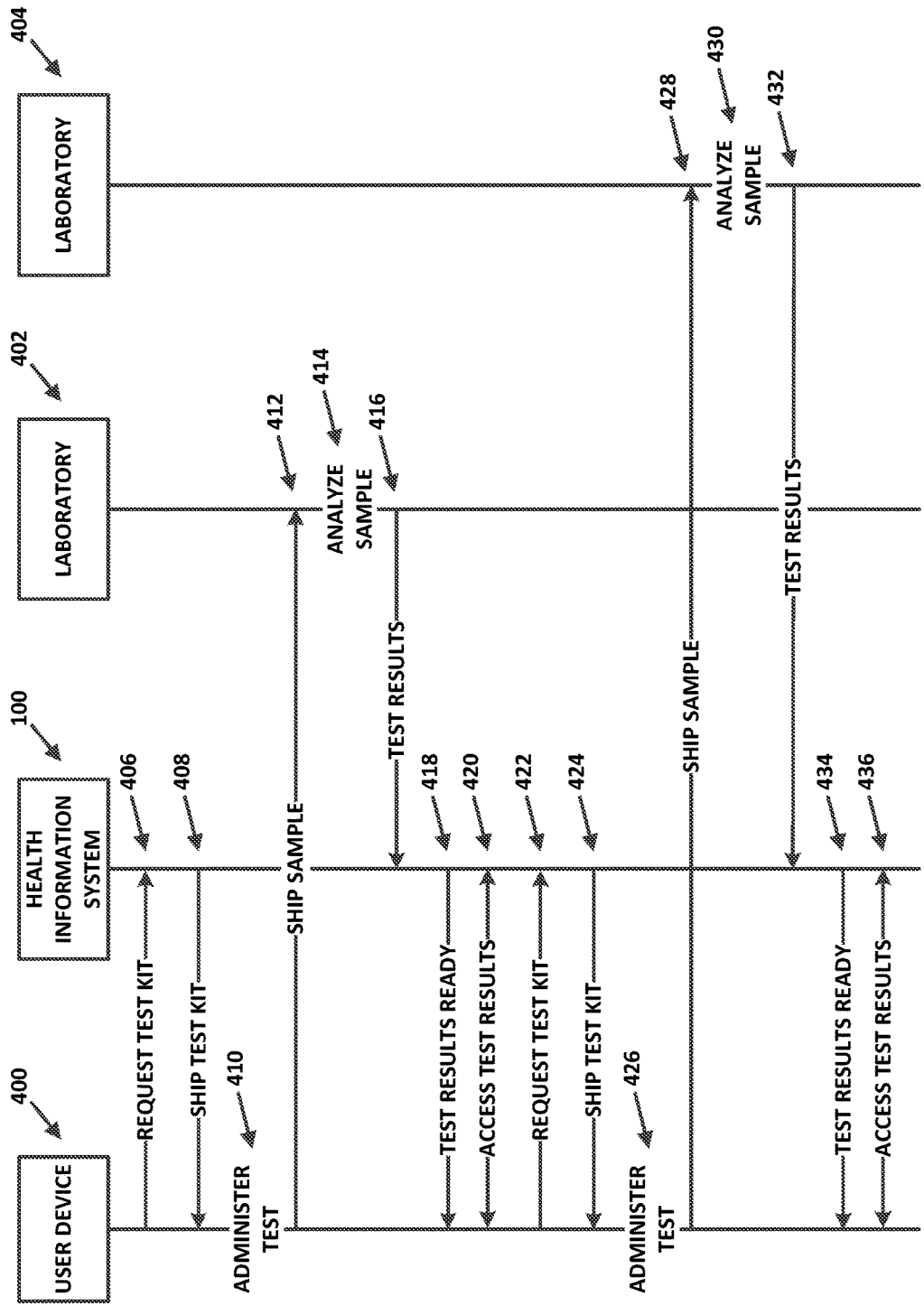
FIG. 4A is an information flow diagram, according to an example embodiment.

FIG. 4A is an example ecommerce information flow that may be supported by health information system 100. Health information system 100 may provide an online ecommerce portal at which various types of home health test kits can be ordered. User device 400, one of user devices 112, may be in communication with health information system 100. Laboratory 402 and laboratory 404 may also be in communication with health information system 100. These laboratories may be arranged to analyze test samples (e.g., blood samples, saliva samples, skin samples, etc.). Each of these entities may communicate with one another via a computer network such as the Internet.

In traditional health care, a patient (e.g., user) typically attends an appointment with a medical professional (e.g., a doctor) in order to obtain a health test (e.g., a blood sample, saliva sample, skin samples, etc.). The medical professional may either collect a sample from the patient or send the patient to a laboratory for sample collection. Once the sample is collected, the laboratory (which may have been selected by the medical professional), analyzes the sample and sends the test results to the medical professional. The user obtains information regarding the test results from the medical professional, and may not be granted access to the raw test results.

Some users may prefer to have more privacy and control over their health care and medical information. Instead of, or in addition to visiting a medical professional, these users may order home health test kits. The test kits may be provided by health information system 100 directly, or by an entity associated with the operation of health information system 100 or a laboratory.

The users may also be able choose which of several possible laboratories to send the sample collected by these kits, and the selected laboratories may have the capability to upload test results directly to health information system 100 (e.g., update or post the results to health information system 100 via an appropriate API). In this way, the user has access to, privacy over, and controls their own health information, and the entire procedure revolves around the user instead of the medical professional. Alternatively, the user may order a test kit that is associated with a particular laboratory, and then may send the sample to that laboratory.

Accordingly, at step 406, user device 400, on behalf of a user with an account on health information system 100, may transmit a request for a test kit to health information system 100. At step 408, health information system 100 may ship (e.g., via postal mail) the requested test kit to the user. In some embodiments, health information system 100 may forward the request for the test kit to a laboratory (e.g., laboratory 402 or laboratory 404), and the laboratory may ship the test kit directly to the user or via health information system 100.

At step 410, the user may administer the test, and at step 412, may ship a test sample (again, possibly by postal mail) to a laboratory, such as laboratory 402. At step 414, laboratory 402 may analyze the sample, and at step 416 may upload (or post via an API supported by health information system 100) the test results to health information system 100.

Possibly in response to receiving this upload, at step 418, health information system 100 may transmit a message to user device 400 that the test rests are ready. Then, at step 420, the user of user device 400 may access the test results.

In some situations, the user might want to use multiple laboratories for different tests. For instance, some laboratories may have a reputation for providing more accurate results for specific types of tests. Alternatively, the user might want to have two or more laboratories analyze the same types of samples so that the user can corroborate each laboratory's results. For instance, the user may draw two blood samples, and send each one to a different laboratory.

Thus, at step 422, user device 400, on behalf of the user, may transmit a request for a test kit to health information system 100. At step 424, health information system 100 may ship the requested test kit to the user. The test kit may be the same type of test kit as was shipped in step 408, or may be a different type of test kit. Health information system 100 may forward the request for the test kit to a laboratory (e.g., laboratory 402 or laboratory 404), and the laboratory may ship the test kit directly to the user or via health information system 100.

At step 426, the user may administer the test, and at step 428, may ship a test sample (again, possibly by postal mail) to a laboratory, such as laboratory 404. At step 430, laboratory 404 may analyze the sample, and at step 432, may upload (or post via an API supported by health information system 100) the test results to health information system 100.

Possibly in response to receiving this upload, at step 434, health information system 100 may transmit a message to user device 400 that the test rests are ready. Then, at step 436, the user of user device 400 may access the test results.

The test results for either test may be raw test results, in that they may be original data from the laboratory with reference ranges and/or little to no interpretation. Possibly though analysis by health information system 100, the raw test results may be accompanied by an interpreted version of the test results, perhaps providing user-friendly explanations and/or highlights of the outcome of the test. User experience module 110 of health information system 100 may allow the user to view both the raw test results from the laboratory and user-friendly, interpreted results provided by health information system 100, perhaps with the ability to switch between views of the two.

Once test results are uploaded to health information system 100, the user may grant other parties access to at least some of this information. For instance, the user may grant access to the test results to medical professionals, family members, and/or friends.

In some embodiments, the user may first obtain an order for a test from a medical professional. The user may upload this order to his or her account, and then this information may be provided along with test kits requests 406 and 422.

Figure 4B:
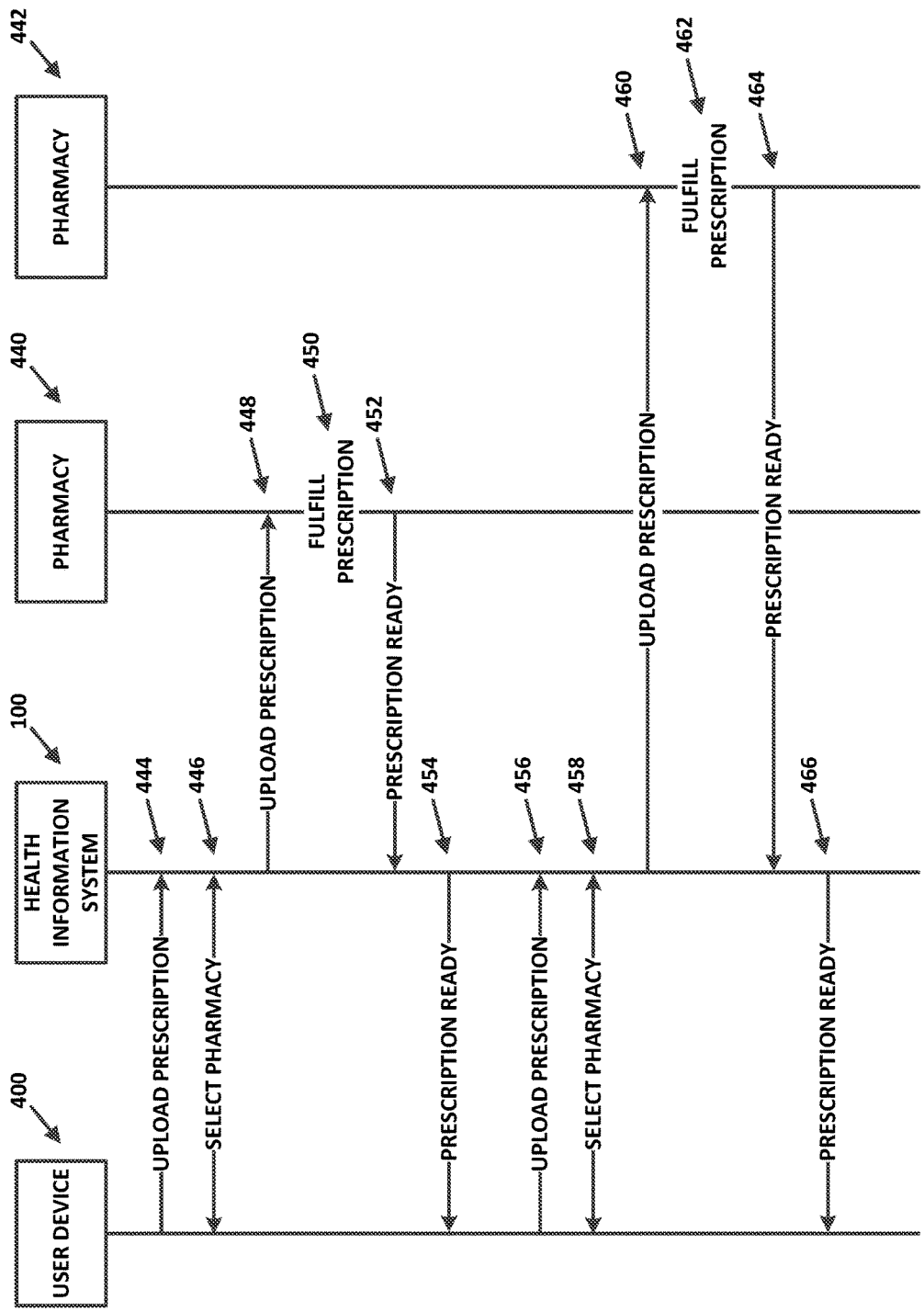
FIG. 4B is an information flow diagram, according to an example embodiment.

FIG. 4B is another example ecommerce information flow that may be supported by health information system 100. Health information system 100 may serve as an intermediary between the user and one or more pharmacies. Thus, pharmacy 440 and pharmacy 442 may also be in communication with health information system 100. These pharmacies may online or physical stores that fulfill prescriptions.

At step 444, user device 400 may upload a prescription to health information system 100. The prescription might entail, for example, a doctor's order to provide the user with a particular medicine or drug. At step 446, via user device 400 and health information system 100, the user may select a pharmacy to fulfill the prescription. Health information system 100 may, for instance, recommend a particular pharmacy based on its location, the cost to fulfill the prescription, supported insurance plans, and/or user preference. Thus, health information system 100 may be arranged to automatically cross-reference or check prescription pricing, prescription ingredients, pharmacy location, and so on according to what is most important to the user, and then provide a list of one or more recommended pharmacies.

At step 448, health information system 100 may upload the prescription to a selected pharmacy, such as pharmacy 440. At step 450, pharmacy 440 may fulfill the prescription, and at step 452, pharmacy 440 may transmit an indication to health information system 100 that the prescription is ready. At step 454, health information system 100 may, in turn, transmit an indication to user device 400 that the prescription is ready (e.g., a push notification to the user's email or mobile device). The user may then choose to pick up the prescription in person or to have the prescription shipped to his or her location.

As was the case with laboratories, health information system 100 may support multiple pharmacies. For instance, the user might prefer to use a primary pharmacy when at home, but select a different one when he or she is travelling. Alternatively or additionally, different pharmacies may charge different amounts to fulfill the same prescription.

Thus, the user might use one pharmacy to fulfill some prescriptions, but use another pharmacy to fulfill additional prescriptions.

Accordingly, at step 456, user device 400 may upload another prescription to health information system 100. At step 458, via user device 400 and health information system 100, the user may select a pharmacy to fulfill the prescription. At step 460, health information system 100 may upload the prescription to a selected pharmacy, such as pharmacy 442. At step 462, pharmacy 442 may fulfill the prescription, and at step 464, pharmacy 442 may transmit an indication to health information system 100 that the prescription is ready. At step 466, health information system 100 may, in turn, transmit an indication to user device 400 that the prescription is ready. The user may then choose to pick up the prescription in person or to have the prescription shipped to his or her location.

Figure 5:
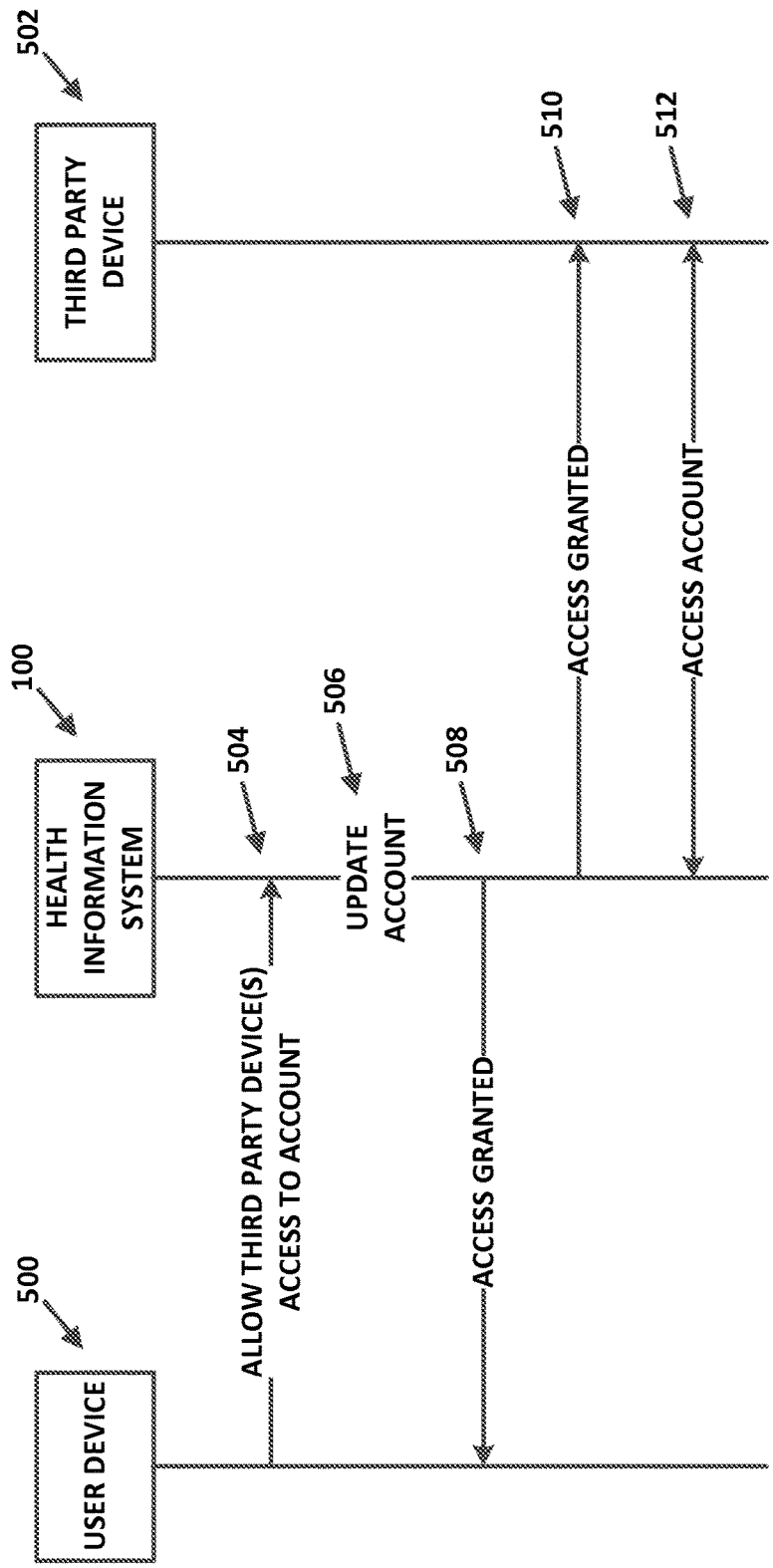
FIG. 5 is an information flow diagram, according to an example embodiment.

FIG. 5 is an example third party authorization information flow that may be supported by health information system 100. In FIG. 5, user device 500, one of user devices 112, may be in communication with health information system 100. Also, third party device 502, one of third party devices 114, may be in communication with health information system 100.

At step 504, user device 500 may allow one or more third party devices access to an account associated with user device 500. Thus, user device 500 may seek to grant third party device 502 access to the account.

At step 506, health information system 100 may update the account to indicate that third party device 502 and/or another account that is associated with third party device 502 is permitted to access parts of the account. At step 508, health information system 100 may transmit an indication to user device 500 that this access has been granted. Similarly, at step 510, health information system 100 may transmit an indication to third party device 502 that this access has been granted.

Then, at step 512, third party device 502 may access the account. This access may entail viewing and/or downloading test results stored in or available via the account.

Additionally, the user may be able to access a medical, health, and/or lifestyle expert via health information system 100. For instance as part of received test results, or after receiving the test results, the user may be presented with an option to review these results with an expert, or otherwise contact an expert. This contact may be via health information system 100, phone, text message, email, video call, etc.

Any of these embodiments may also be used for purposes of pet health as well. Thus, users may browse and order pet health test kits, obtain laboratory results, and share these results with veterinarians and other entities. In these cases, the information in user accounts 102 and general data 104 may include pet-related data.

4. EXAMPLE INFORMATION STORED IN A HEALTH INFORMATION SYSTEM

Possibly as part of an account of a particular user in user accounts 102, or part of general data 104, various types of data may be stored or accessible. This data may be in addition to test results, and may be divided into various categories, included or not limited to the following.

a. Manually Inputted Data

An account of user accounts 102 may include data related to a user's food, diet and nutrition, sleep, sexual activities, stress, fitness, exercise and activity, height, weight, hydration, blood sugar, blood pressure, other blood works, cholesterol, heart rate, respiratory rate, oxygen saturation, anger levels, female fertility and ovulation, female menstrual cycles, emotional and mental health, religion and spiritual health, social connections and social health, medical history, conditions and disease, doctors, hospitals and visit history, children's health, spouse health, baby health, and notes from friends, family, doctors, health practitioners.

b. Data from Monitoring Devices

An account of user accounts 102 may include data that can be collected via various types of health tracking and monitoring devices. These devices may include wearable computing devices, such as digital pedometers, heart rate monitors, and so on. Thus, data may be collected via wristbands, healthbands, watches, smartwatches, headbands, socks, shirts, fashion apparel, tricoders, home tracking devices, thermometers, diabetes and blood sugar monitoring devices, bandages, smartphones, smart wallets, children and baby monitors, children and baby fashion apparel, fashion accessories (e.g., bags, belts, pins, buttons, cuff links, scarves, etc.), textiles, eyewear, fashion, jewelry (necklaces, earrings, bracelets, etc.), bikes, electronic audio devices, cameras, sousveillance (data collection units worn by an individual), ear pieces, hearing aids, and so on.

c. General Data

Possibly as part of general data 104, health information system 100 may store or have access to various types of general information. This information may include, but is not limited to, health-related articles, academic papers, personal stories, advice from experts, links to other web sites, and so on.

5. EXAMPLE ANALYTICS

Analytics engine 106 may include various capabilities to analyze the data associated with an account, as well as general data 104, to draw conclusions from this information. Two example embodiments are provided below, one a correlation analysis and the other a longitudinal trend analysis. However, these embodiments are merely examples, and other embodiments may exist, and these embodiments may use correlational analysis, longitudinal trend analysis, a combination of both, or one or more additional techniques.

a. Correlations

Figure 6:
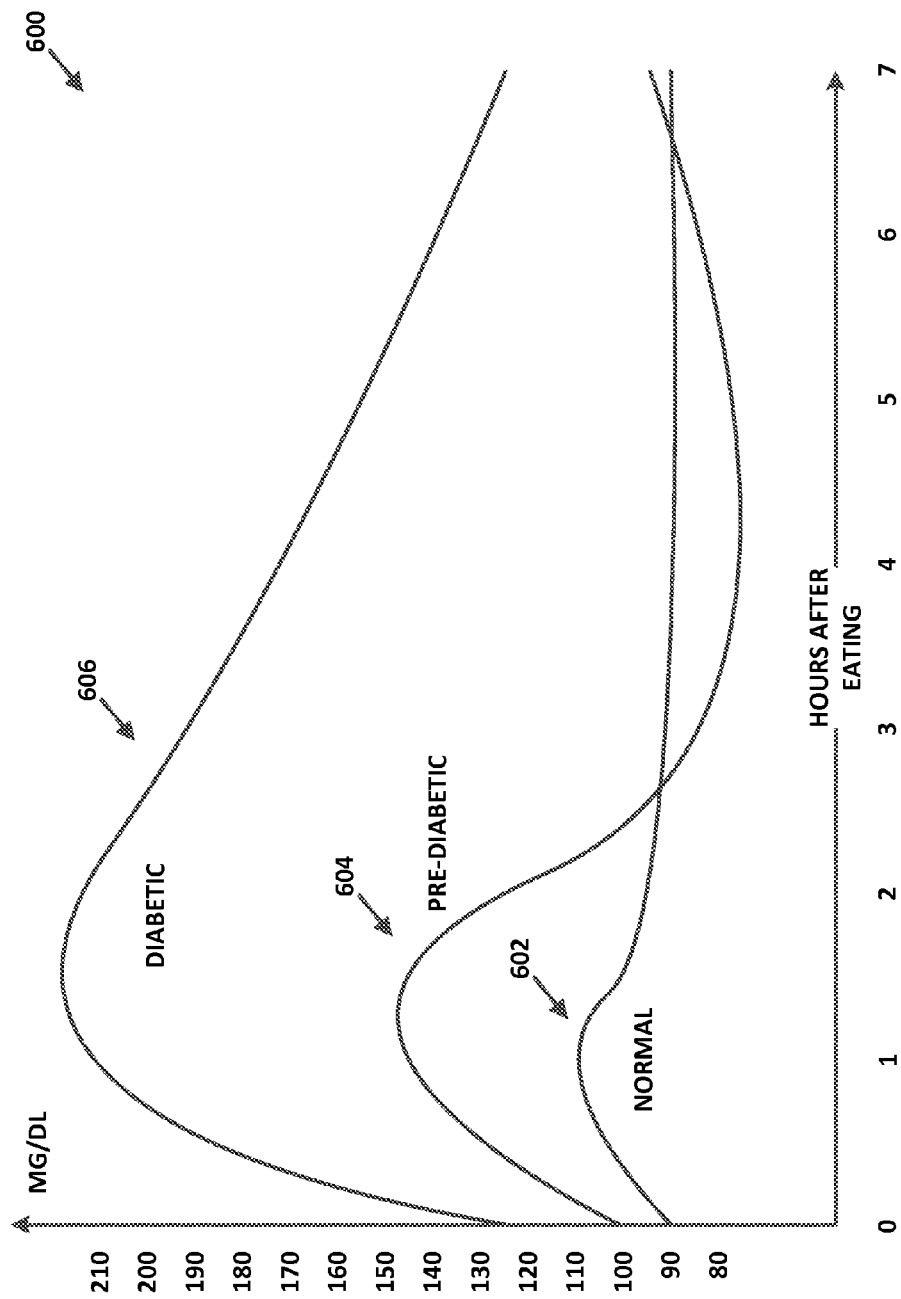
FIG. 6 is a correlational analysis chart, according to an example embodiment.

FIG. 6 illustrates example data that could be used in a correlation analysis. Chart 600 is a graph that plots blood sugar levels versus the number of hours after eating a meal. Three example curves are plotted. Curve 602 indicates a normal blood sugar response, which starts at about 90 milligrams per deciliter (mg/dL) and peaks around 110 mg/dL one hour after eating, then fall back to 90 mg/dL. Curve 604 indicates a pre-diabetic blood sugar response, which starts at about 100 mg/dL, peaks around 150 mg/dL approximately 1.5 hours after eating, dips below 80 mg/dL for several hours after that, then returns to about 100 mg/dL. Curve 606 indicates a diabetic blood sugar response, which starts at about 125 mg/dL, peaks around 215 mg/dL approximately 2 hours after eating, and then returns to about 125 mg/dL.

Analytics engine 106 may use these curves to determine a likelihood of diabetes in a user. For instance, the user might be wearing a device that periodically measures the user's blood sugar levels. Alternatively, the user may manually test his or her blood sugar levels several times after eating. The time that the user ate the meal could also be manually or automatically collected.

Based on data points collected from the user, analytics engine 106 may compare the data points to curve 602, 604, and 606. For instance, analytics engine may conduct a regression analysis to determine a curve for the data points, and/or perform one or more goodness-of-fit tests between data collected from the user and these curves. Based on the outcome of these tests, analytics engine may conclude that the data points are more likely to indicate a normal response, pre-diabetic response, or a diabetic response, and the user may be informed accordingly.

b. Longitudinal Trends

Figure 7:
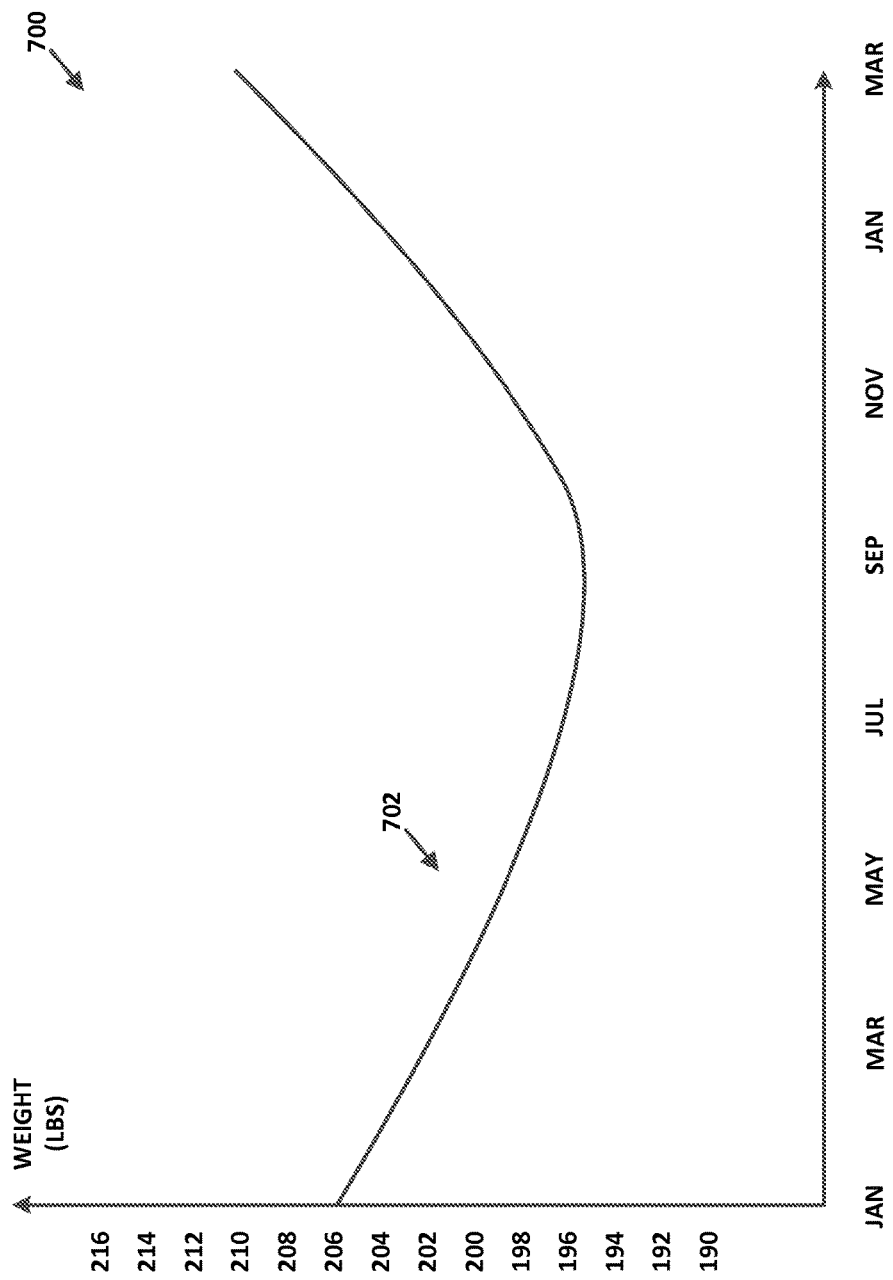
FIG. 7 is a longitudinal trend analysis chart, according to an example embodiment.

FIG. 7 illustrates example data that could be used in a longitudinal trend analysis. Chart 700 plots a male user's weight versus month over a period of 15 months. Curve 702 indicates that the user weighed about 206 pounds in January, and then lost weight steadily that year until about September. In September, the user's weight was about 195 pounds, but over the next six months, the user gained approximately 15 pounds until he weighed about 210 pounds in March of the next year.

Analytics engine 106 may obtain data regarding the user's weight at various points in time (e.g., once a day, one a week, twice a month, etc.) from, for instance, a digital scale or via manual entry. Analytics engine 106 may consider this data over the course of weeks, months, or years to determine the user's weight trends. The particular trend in FIG. 7 may indicate that the user gains weight in the winter months and loses it in the summer. Thus, analytics engine might recommend that the user more carefully plan his diet during the winter as well as obtain more physical activity during these months.

6. EXAMPLE OPERATIONS

Figure 8:
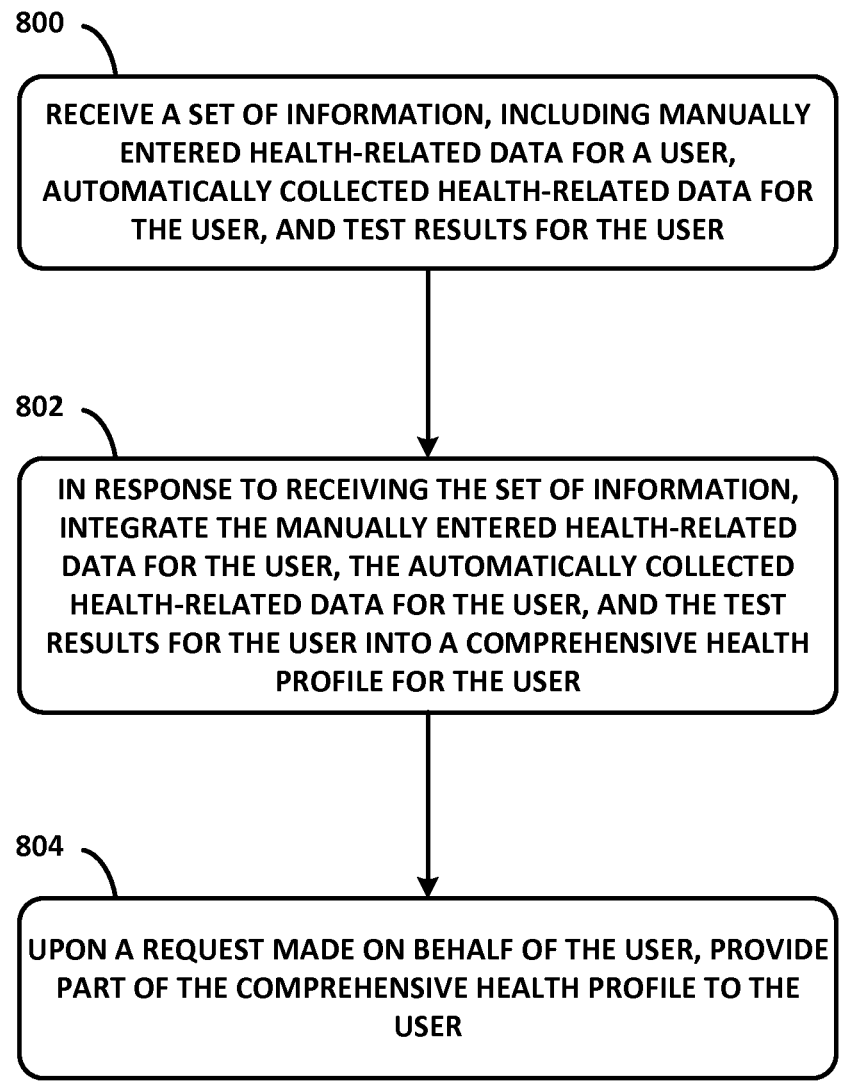
FIG. 8 is a flow chart, according to an example embodiment.

FIG. 8 is a flow chart illustrating an example embodiment. The process illustrated by FIG. 8 may be carried out by a computing device, such as computing device 200, and/or a cluster of computing devices, such as server cluster 304. However, the process can be carried out by other types of devices or device subsystems. For example, the process could be carried out by a portable computer, such as a laptop or a tablet device. Further, the process may be combined with one or more features disclosed in the context of any previous figure.

At block 800, a computing device may receive a set of information including manually entered health-related data for a user, automatically collected health-related data for the user, and test results for the user. In some cases, the computing device may collect this information from various sources.

At block 802, in response to receiving the set of information, the computing device may integrate the manually entered health-related data for the user, the automatically collected health-related data for the user, and the test results for the user into a comprehensive health profile for the user. At block 804, upon a request made on behalf of the user, the computing device may provide part of the comprehensive health profile to the user.

The test results for the user may be based on a first test and a second test. The first test may be performed by a first laboratory and the second test may be performed by a second laboratory. The first laboratory and the second laboratory may be independent from one another.

Receiving the test results for the user may involve receiving a first request for the first test for the user and facilitating shipment of a first kit for the first test to the user. The first test kit may include instructions to use the first kit and to provide a first sample for the first test to the first laboratory. First results of the first test may be received from the first laboratory.

Receiving the test results for the user may also involve receiving a second request for the second test for the user and facilitating shipment of a second kit for the second test to the user. The second test kit may include instructions to use the second kit and to provide a second sample for the second test to the second laboratory. Second results of the second test may be received from the second laboratory.

In some embodiments, integrating the manually entered health-related data for the user, the automatically collected health-related data for the user, and the test results for the user into the comprehensive health profile for the user may involve determining at least one health-related correlation between any two of the manually entered health-related data for the user, the automatically collected health-related data for the user, and the test results for the user. This integration may further involve adding an indication of the health-related correlation to the comprehensive health profile for the user.

Alternatively or additionally, integrating the manually entered health-related data for the user, the automatically collected health-related data for the user, and the test results for the user into the comprehensive health profile for the user may involve determining one or more longitudinal trends regarding one or more of the manually entered health-related data for the user, the automatically collected health-related data for the user, and the test results for the user. This integration may further involve adding an indication of the one or more longitudinal trends to the comprehensive health profile for the user.

The manually entered health-related data for the user may include nutritional information about the user and/or medical questionnaire answers from the user. The automatically collected health-related data for the user may include physical activity information of the user and/or biometric data of the user.

The example embodiment of FIG. 8 may further include receiving authorization from the user to allow a second user to access at least part of the comprehensive health profile for the user, and modifying the comprehensive health profile for the user to allow the second user to access at least part of the comprehensive health profile for the user. Additionally, a request may be received from the second user to access the at least part of the comprehensive health profile for the user, and a representation of the at least part of the comprehensive health profile for the user may be transmitted to the second user.

7. CONCLUSION

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages can be executed out of order from that shown or discussed, including substantially concurrent or in reverse order, depending on the functionality involved. Further, more or fewer blocks and/or functions can be used with any of the ladder diagrams, scenarios, and flow charts discussed herein, and these ladder diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical functions or actions in the method or technique. The program code and/or related data can be stored on any type of computer readable medium such as a storage device including a disk, hard drive, or other storage medium.

The computer readable medium can also include non-transitory computer readable media such as computer-readable media that store data for short periods of time like register memory, processor cache, and random access memory (RAM). The computer readable media can also include non-transitory computer readable media that store program code and/or data for longer periods of time. Thus, the computer readable media may include secondary or persistent long term storage, like read only memory (ROM), optical or magnetic disks, compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

I claim:

1. A method comprising:

receiving, by a server device, a set of information including pluralities of data points for each of manually entered health-related data for a user, automatically collected health-related data for the user, and medical test results for the user, wherein the server device receives the automatically collected health-related data periodically via a network from a wearable health-tracking device worn by the user;

in response to receiving the set of information, integrating, by the server device, the manually entered health-related data for the user, the automatically collected health-related data for the user, and the medical test results for the user into a comprehensive health profile for the user, wherein integrating the manually entered health-related data for the user, the automatically collected health-related data for the user, and the medical test results for the user into the comprehensive health profile for the user comprises:

(i) determining a health-related correlation between diet, medication intake, and reported mood of the user, wherein the health-related correlation indicates an extent to which respective data points related to the diet, medication intake, and reported mood of the user vary together, (ii) adding an indication of the health-related correlation to the comprehensive health profile for the user, (iii) performing, by an analytics engine, goodness-of-fit tests between (a) a series of blood sugar levels from the user measured at points in time after the user has eaten, and (b) curves representing each of a normal blood sugar response after eating, a pre-diabetic blood sugar response after eating, and a diabetic blood sugar response after eating, wherein the series of blood sugar levels from the user is part of the one or more of the manually entered health-related data for the user, the automatically collected health-related data for the user, and the medical test results for the user, (iv) based on the goodness-of-fit tests, concluding, by the analytics engine, that the series of blood sugar levels from the user indicates the normal blood sugar response after eating, the pre-diabetic blood sugar response after eating, or the diabetic blood sugar response after eating, (v) adding an indication of the conclusion to the comprehensive health profile for the user, (vi) determining one or more longitudinal trends regarding one or more of the manually entered health-related data for the user, the automatically collected health-related data for the user, and the medical test results for the user, wherein the one or more longitudinal trends include a longitudinal trend of a weight of the user that indicates that the user gains weight during a particular season, (vii) adding an indication of the one or more longitudinal trends to the comprehensive health profile for the user, and (viii) determining, by the analytics engine, a seasonal diet and exercise recommendation for the user based on the longitudinal trend; and upon a request made on behalf of the user, providing, by the server device, part of the comprehensive health profile, including a result of the goodness-of-fit tests or the seasonal diet and exercise recommendation, to the user.

2. The method of claim 1, wherein the medical test results for the user are based on a first test and a second test, wherein the first test was performed by a first laboratory and the second test was performed by a second laboratory, and wherein the first laboratory and the second laboratory are independent from one another, the method further comprising:

corroborating results of the first test with results of the second test.

3. The method of claim 2, wherein receiving the medical test results for the user comprises:

receiving, by the server device, a first request for the first test for the user;

facilitating, by the server device, shipment of a first kit for the first test to the user, with instructions to use the first kit and to provide a first sample for the first test to the first laboratory; and receiving, by the server device, first results of the first test from the first laboratory.

4. The method of claim 3, wherein receiving the medical test results for the user comprises:

receiving, by the server device, a second request for the second test for the user;

facilitating, by the server device, shipment of a second kit for the second test to the user, with instructions to use the second kit and to provide a second sample for the second test to the second laboratory; and receiving, by the server device, second results of the second test from the second laboratory.

5. The method of claim 1, wherein the manually entered health-related data for the user includes medical questionnaire answers from the user.

6. The method of claim 1, wherein the automatically collected health-related data for the user includes physical activity information of the user.

7. The method of claim 1, further comprising:

receiving, by the server device, authorization from the user to allow a second user to access at least part of the comprehensive health profile for the user;

modifying, by the server device, the comprehensive health profile for the user to allow the second user to access at least part of the comprehensive health profile for the user;

receiving, by the server device, a request from the second user to access the at least part of the comprehensive health profile for the user; and transmitting, by the server device, a representation of the at least part of the comprehensive health profile for the user to the second user.

8. An article of manufacture including a non-transitory computer-readable medium, having stored thereon program instructions that, upon execution by a server device, cause the server device to perform operations comprising:

receiving a set of information including pluralities of data points for each of manually entered health-related data for a user, automatically collected health-related data for the user, and medical test results for the user, wherein the server device receives the automatically collected health-related data periodically via a network from a wearable health-tracking device worn by the user;

in response to receiving the set of information, integrating the manually entered health-related data for the user, the automatically collected health-related data for the user, and the medical test results for the user into a comprehensive health profile for the user, wherein integrating the manually entered health-related data for the user, the automatically collected health-related data for the user, and the medical test results for the user into the comprehensive health profile for the user comprises:

(i) determining a health-related correlation between diet, medication intake, and reported mood of the user, wherein the health-related correlation indicates an extent to which respective data points related to the diet, medication intake, and reported mood of the user vary together, (ii) adding an indication of the health-related correlation to the comprehensive health profile for the user, (iii) performing, by an analytics engine, goodness-of-fit tests between (a) a series of blood sugar levels from the user measured at points in time after the user has eaten, and (b) curves representing each of a normal blood sugar response after eating, a pre-diabetic blood sugar response after eating, and a diabetic blood sugar response after eating, wherein the series of blood sugar levels from the user is part of the one or more of the manually entered health-related data for the user, the automatically collected health-related data for the user, and the medical test results for the user, (iv) based on the goodness-of-fit tests, concluding, by the analytics engine, that the series of blood sugar levels from the user indicates the normal blood sugar response after eating, the pre-diabetic blood sugar response after eating, or the diabetic blood sugar response after eating, (v) adding an indication of the conclusion to the comprehensive health profile for the user, (vi) determining one or more longitudinal trends regarding one or more of the manually entered health-related data for the user, the automatically collected health-related data for the user, and the medical test results for the user, wherein the one or more longitudinal trends include a longitudinal trend of a weight of the user that indicates that the user gains weight during a particular season, (vii) adding an indication of the one or more longitudinal trends to the comprehensive health profile for the user, and (viii) determining, by the analytics engine, a seasonal diet and exercise recommendation for the user based on the longitudinal trend; and upon a request made on behalf of the user, providing part of the comprehensive health profile, including a result of the goodness-of-fit tests or the seasonal diet and exercise recommendation, to the user.

9. The article of manufacture of claim 8, wherein the medical test results for the user are based on a first test and a second test, wherein the first test was performed by a first laboratory and the second test was performed by a second laboratory, and wherein the first laboratory and the second laboratory are independent from one another, the operations further comprising:

corroborating results of the first test with results of the second test.

10. The article of manufacture of claim 9, wherein receiving the medical test results for the user comprises:

receiving a first request for the first test for the user;

facilitating shipment of a first kit for the first test to the user, with instructions to use the first kit and to provide a first sample for the first test to the first laboratory; and receiving first results of the first test from the first laboratory.

11. The article of manufacture of claim 10, wherein receiving the medical test results for the user comprises:

receiving a second request for the second test for the user;

facilitating shipment of a second kit for the second test to the user, with instructions to use the second kit and to provide a second sample for the second test to the second laboratory; and receiving second results of the second test from the second laboratory.

12. A server device comprising:

at least one processor;

data storage; and program instructions, stored in the data storage, that upon execution by the at least one processor cause the server device to perform operations including:

receiving a set of information including pluralities of data points for each of manually entered health-related data for a user, automatically collected health-related data for the user, and medical test results for the user, wherein the server device receives the automatically collected health-related data periodically via a network from a wearable health-tracking device worn by the user;

in response to receiving the set of information, integrating the manually entered health-related data for the user, the automatically collected health-related data for the user, and the medical test results for the user into a comprehensive health profile for the user, wherein integrating the manually entered health-related data for the user, the automatically collected health-related data for the user, and the medical test results for the user into the comprehensive health profile for the user comprises:

(i) determining a health-related correlation between diet, medication intake, and reported mood of the user, wherein the health-related correlation indicates an extent to which respective data points related to the diet, medication intake, and reported mood of the user vary together, (ii) adding an indication of the health-related correlation to the comprehensive health profile for the user, (iii) performing, by an analytics engine, goodness-of-fit tests between (a) a series of blood sugar levels from the user measured at points in time after the user has eaten, and (b) curves representing each of a normal blood sugar response after eating, a pre-diabetic blood sugar response after eating, and a diabetic blood sugar response after eating, wherein the series of blood sugar levels from the user is part of the one or more of the manually entered health-related data for the user, the automatically collected health-related data for the user, and the medical test results for the user, (iv) based on the goodness-of-fit tests, concluding, by the analytics engine, that the series of blood sugar levels from the user indicates the normal blood sugar response after eating, the pre-diabetic blood sugar response after eating, or the diabetic blood sugar response after eating, (v) adding an indication of the conclusion to the comprehensive health profile for the user, (vi) determining one or more longitudinal trends regarding one or more of the manually entered health-related data for the user, the automatically collected health-related data for the user, and the medical test results for the user, wherein the one or more longitudinal trends include a longitudinal trend of a weight of the user that indicates that the user gains weight during a particular season, (vii) adding an indication of the one or more longitudinal trends to the comprehensive health profile for the user, and (viii) determining, by the analytics engine, a seasonal diet and exercise recommendation for the user based on the longitudinal trend; and upon a request made on behalf of the user, providing part of the comprehensive health profile, including a result of the goodness-of-fit tests or the seasonal diet and exercise recommendation, to the user.

13. The server device of claim 12, wherein the medical test results for the user are based on a first test and a second test, wherein the first test was performed by a first laboratory and the second test was performed by a second laboratory, and wherein the first laboratory and the second laboratory are independent from one another, the operations further including:

corroborating results of the first test with results of the second test.

14. The server device of claim 13, wherein receiving the medical test results for the user comprises:

receiving a first request for the first test for the user;

facilitating shipment of a first kit for the first test to the user, with instructions to use the first kit and to provide a first sample for the first test to the first laboratory; and receiving first results of the first test from the first laboratory.

15. The server device of claim 14, wherein receiving the medical test results for the user comprises:

receiving a second request for the second test for the user;

facilitating shipment of a second kit for the second test to the user, with instructions to use the second kit and to provide a second sample for the second test to the second laboratory; and receiving second results of the second test from the second laboratory.

* * * * *